United States Patent [19]

Kaluza et al.

[11] Patent Number: 5,134,069
[45] Date of Patent: Jul. 28, 1992

[54] TYPE II RESTRICTION ENDONUCLEASE SGRAI

[75] Inventors: Klaus Kaluza, Bad Heilbrunn; Bruno Frey, Penzberg; Gudrun Schmitz-Agheguian, Bernried; Michael Jarsch, Bad Heilbrunn; Christoph Kessler, Dorfen, all of Fed. Rep. of Germany

[73] Assignee: Boehringer Mannheim GmbH, Mannheim, Fed. Rep. of Germany

[21] Appl. No.: 615,439

[22] Filed: Nov. 16, 1990

[30] Foreign Application Priority Data

Nov. 16, 1989 [DE] Fed. Rep. of Germany ....... 3938143

[51] Int. Cl.$^5$ ......................... C12P 19/34; C12N 9/22
[52] U.S. Cl. ....................................... 435/91; 435/199; 435/897
[58] Field of Search .................. 435/199, 91

[56] References Cited

PUBLICATIONS

Tautz, N., et al. (1990), Nuc. Acids Res. 18(10), 3087.
Laue, F., et al. (1990) Nuc. Acids Res. 18(11), 3421.
Tautz, N., et al, (1990), Nuc. Acid Res. 18(16), 4991.

Primary Examiner—Charles L. Patterson, Jr.
Attorney, Agent, or Firm—Felfe & Lynch

[57] ABSTRACT

The type III restriction endonuclease SgrAI has the following recognition sequence:

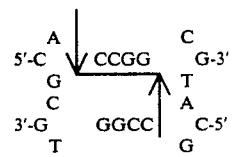

cleaves DNA at the cleavage site indicated by the arrows, and is preferably obtainable from microorganisms of the genus Streptomyces. It can be used to recognize and cleave the double-stranded DNA sequence

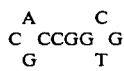

and its complementary sequence.

10 Claims, No Drawings

TYPE II RESTRICTION ENDONUCLEASE SGRAI

FIELD OF THE INVENTION

The invention concerns the type II restriction endonuclease SgrAI, a process for its isolation and its use.

BACKGROUND AND PRIOR ART

Type II restriction endonucleases are endodeoxyribonucleases which recognize and cleave particular DNA sequences. In this process one phosphodiester bridge is hydrolyzed in each polynucleotide strand of the target sequence. Type II restriction endonucleases are thus of value for the analysis of DNA molecules. Although type II restriction endonucleases are known which are specific for numerous DNA sequences, there is still a need for further restriction endonucleases with new specificities.

SUMMARY OF THE INVENTION

The present invention is a type II restriction endonuclease having the recognition sequence

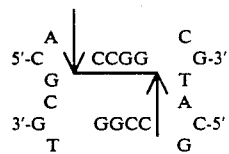

and the cleavage site defined by the arrows.

DETAILED DESCRIPTION OF PREFERRED EMBODIMENTS

The new restriction endonuclease according to the present invention, which is denoted SgrAI hereafter, has a temperature optimum at ca. 37° C. The enzyme has good activity between pH 7.5 and pH 8.5 in 33 mmol/l Trisacetate buffer with 10 mmol/l $MgCl_2$, 66 mmol/l $CH_3COOK$ and 1.0 mmol/l DTE (dithioerythritol). The pH optimum is at ca. pH 7.9. An enzyme which has the same recognition sequence and cleavage site as SgrAI is not known. The recognition sequence can be confirmed by the complete digestion of the DNA of the SV40 and adeno 2 viruses, of phage lambda and phage phiX174 and of the phage derivative M13mp8 and of the pBR322 and pBR328 plasmids. These DNA molecules are treated with SgrAI.

Table 1 shows a comparison of the cleavage site specificity observed with a cleavage site specificity determined by a computer for an enzyme which recognizes the following sequence:

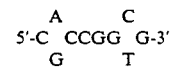

TABLE 1

| DNA | Fragment lengths determined experimentally [bp] | Fragment lengths determined by computer analysis [bp] | Cleavage positions determined by computer analysis (at the base pairs) | Number of cleavage sites determined by computer analysis | Number of cleavage sites determined experimentally |
|---|---|---|---|---|---|
| SV 40 | 0 | 0 | 0 | 0 | 0 |
| M13mp8 | 0 | 0 | 0 | 0 | 0 |
| phiX174 | 0 | 0 | 0 | 0 | 0 |
| pBR322 | 4400 | 4363 | 408 | 1 | 1 |
| pBR328 | 4900 | 4907 | 409 | 1 | 1 |
| Lambda | 17000, 15000, 7000, 4200, 2800, 1600, 1300 | 16679, 14850, 7063, 4198, 2775, 1616, 1321 | 7064, 8680, 12878, 15653, 16974, 31824 | 6 | 6 |
| Ad | 17000, 9200, 6000, 2700, 630, 330, 180 | 16978, 9175, 5915, 2727, 625, 334, 184 | 184, 808, 17786, 23701, 26428, 26762 | 6 | 6 | bp: base pair(s)

The cleavage position within the recognition sequence of the enzyme can be determined on a M13 derivative having this recognition sequence at an interval of ca. 30-200 bases from the binding site of the universal sequencing primer (Messing, J. et al., (1981) Nucl. Acids Res. 9, 309-321). At first sequencing reactions according to the dideoxy chain-termination method (Sanger, F. et al., (1977) Proc. Natl. Acad. Sci. USA 74, 560-564, Messing, J. et al., (1981) Nucl. Acids Res. 9, 309-321) are carried out on the single-stranded DNA of the M13 derivative with the universal sequencing primer.

Parallel with this, the sequencing primer is radioactively labelled at the 5' end with T4-polynucleotide kinase and [Y-$^{32}$P]ATP. After hybridization of this 5' end-labelled sequencing primer to the single-stranded M 13 DNA, a partially double-stranded DNA is prepared in a "filling in" reaction with DNA-polymerase I (Klenow enzyme) and a deoxynucleotide triphosphate mixture of dATP, dCTP, dGTP and dTTP. An aliquot of this DNA, of which the newly synthesized strand is radioactively labelled at the 5' end, is now cleaved with the restriction endonuclease SgrAI. Half of the cleavage preparation is additionally treated with T4-DNA polymerase in the presence of a mixture of all four deoxynucleotide triphosphates in order to obtain blunt DNA ends.

The analysis of the reaction products is carried out by electrophoresis on sequencing gels (8 mol/l urea, 5 % polyacrylamide) and subsequent autoradiography. The results are interpreted according to Brown, N.L. and Smith, M. (Methods in Enzymology 65 (1980) 391-401). The position of the cleavage site is determined by a comparison of the distances of migration of the radioactively-labelled fragments with the sequencing ladder. The samples which were additionally treated with T4-DNA polymerase show a band which is four base pairs longer in comparison with the samples which were only cleaved with SgrAI. This therefore shows that SgrAI produces a 5' end which protrudes by four base pairs.

SgrAI has therefore the following cleavage specificity within the recognition sequence:

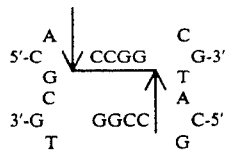

The number of cleavage sites determined experimentally is identical to the number of cleavage sites for the sequence

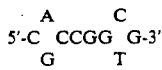

obtained by computer analysis with the different DNA's (Table I). In addition these data were also compared with the tables in Gene 10 (1980) 357-370.

SgrAI is preferably isolated by culturing microorganisms of the genus *Streptomyces*, preferably microorganisms of the species *Streotomyces griseus* and isolating the enzyme from the cells. In particular *Streptomyces griseus* DSM 5621 is preferred. The microorganism *Streptomyces griseus* was deposited at the German Collection for Microorganisms, Gesellschaft für biotechnologische Forschung mbH, Mascheroder Weg 1b, 3300 Braunschweig, BRD and has the deposit number DSM 5621.

The usual biochemical methods of purification can be used for the isolation in which the presence of the enzyme in the respective fractions obtained can be easily tested on the basis of the cleavage of its recognition sequence. Lambda DNA is, for example, suitable as the substrate. The DNA fragments obtained are separated electrophoretically in agarose gels in buffer systems usually used for the fragment separation in the presence of ethidium bromide.

The microorganisms used for the isolation of the enzyme grow aerobically in a M 111 medium (10 g/l yeast extract; 10 g/l malt extract).

The optimal conditions for growth are at 26° C., pH 6.5-7.5. The doubling time is about 2.5 hours.

The enzyme is isolated and purified by the usual chemical and mechanical methods such as, for example, by high pressure dispersion, ultrasound or enzymatic lysis. The cells are preferably lysed by means of a French press. The further purification of the supernatant is preferably carried out by means of affinity chromatography and ion-exchange chromatography. Heparin-Sepharose® CL-6B (Pharmacia) is for example suitable as the material for the affinity chromatography. Cellulose phosphate (Whatman) is for example suitable as the material for cation P11 exchange chromatography.

The product available under the name DEAE Sephacel® (Pharmacia) is suitable as the anion-exchanger. Other chromatographic materials which are known to the expert are also suitable.

The following Examples elucidate the invention further.

EXAMPLE 1

*Streptomyces griseus* DSM 5621 is cultured at 26° C. for 5 hours and is harvested in the logarithmic phase. The culture medium is M 111 medium. The cell paste (30 g wet weight) is resuspended in 2.4 volumes buffer A (40 mmol/l Tris/HCl, pH 8.0, 0.1 mmol/l EDTA, 7 mmol/l 2- mercaptoethanol), which contains protease inhibitors. Subsequently, the cells are lysed by passing then twice through a French press at 23,000 lb/inch² and the precipitate is separated off. To the supernatant NH₄Cl is added (final concentration 0.3 mol/l) and by means of polymin nucleic acids are precipitated and separated off. Subsequently 55 % ammonium sulfate is added to the supernatant which is subsequently fractionated on a heparin-Sepharose column. A gradient of 0-1 mol/l NaCl is used for the elution. SgrAI is found in the fractions between 0.4 and 0.6 mol/l NaCl. The active fractions are dialysed against buffer B (40 mmol/l Tris-HCl; pH 8.0; 0.1 mmol/l EDTA; 7 mmol/l 2-mercaptoethanol; 10 % (w/v) glycerol). Subsequently, they are applied to a DEAE-Sephacel column which was equilibrated with buffer B. A gradient of 0-0.5 mol/l NaCl in buffer B is used for the elution.

The active fractions are dialyzed against buffer B. Subsequently they are applied to a cellulose phosphate column equilibrated with buffer B. A gradient of 0-1 mol/l NaCl in buffer B is used for the elution. SgrAI is found in the fractions between 0.3 and 0.5 mol/l NaCl. The active fractions are pooled and dialyzed against storage buffer (20 mmol/l Tris-Hcl, pH 8.0 , 10 mmol/l 2- mercaptoethanol and 100 mmol/l NaCl, 0.1 mmol/l EDTA and 50% (v/v) glycerol).

EXAMPLE 2

DETERMINATION OF THE ACTIVITY

Definition of the enzyme units: 1 U SgrAI cleaves 1 μg lambda DNA within 1 hour at 37° C. in 25 μl final volume.

17.9 μl water and 3.6 μl lambda DNA (optical density: 5,6 OD/ml) as well as 1 μl SgrAI solution (1 U/μl) are added to a mixture of 2.5 μl incubation buffer (100 mmol/l Tris-HCl, pH 7.5, 37° C., 100 mmol/l magnesium chloride) and 10 mmol/l DTE). The solution is incubated for 1 hour at 37° C., cooled on ice and 5 μl of a terminating reagent consisting of 7 mmol/l urea, 20 % (w/v) sucrose, 60 mmol1 EDTA and 0.06 % (w/v) bromophenol blue is added. Subsequently separation is carried out by electrophoresis in 1 % agarose gels for 3-4 hours at 100 V. The bands obtained are identified by comparison with a DNA length standard.

We claim:

1. Type II restriction endonuclease which recognizes a DNA sequence selected from the group consisting of:

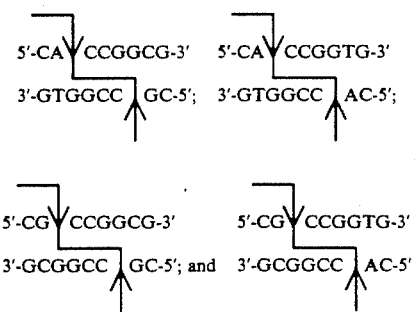

and which cleaves said DNA sequence at a position indicated by the arrows.

2. Restriction endonuclease of claim 1, obtained from microorganisms of the genus *Streptomyces*.

3. Restriction endonuclease of claim 1, obtained from *Streptomyces griseus* DSM 5621.

4. Restriction endonuclease of claim 1 characterized by a temperature optimum of about 37° C. and a pH optimum of about 7.9.

5. Process for the isolation of a type II restriction endonuclease having a recognition sequence selected from the group consisting of:

and cleaving said sequence at a point indicated by the arrows, comprising culturing a microorganism of genus *Streptomyces* which produces said restriction endonuclease under conditions favoring said production, and isolating said restriction endonuclease from said microorganism.

6. Process of claim 5, wherein said microorganism is *Streptomyces griseus* DSM 5621.

7. Process of claim 6, further comprising lysing cells of said microorganism to yield a supernatant and isolating said restriction endonuclease from said supernatant.

8. Process of claim 7, further comprising subjecting said supernatant to affinity chromatography and anion-exchange chromatography to isolate said restriction endonuclease.

9. Process of claim 8, wherein said affinity chromatography is carried out using carrier bound heparin.

10. Method for obtaining a DNA sequence having a terminal nucleotide sequence selected from the group consisting of:

$$5'\text{-CA-}3' \quad 5'\text{-CCGGCG-}3' \quad 5'\text{-CCGGTG-}3'$$
$$3'\text{-GTGGCC-}5'; \quad 3'\text{-GC-}5'; \quad 3'\text{-AC-}5'; \text{ and}$$

$$5'\text{-CG-}3'$$
$$3'\text{-GCGGCC-}5'$$

comprising contacting a DNA-containing sample with the restriction endonuclease of claim 1 and separating cleavage products produced thereby.

* * * * *

UNITED STATES PATENT AND TRADEMARK OFFICE
CERTIFICATE OF CORRECTION

PATENT NO. : 5,134,069
DATED     : July 28, 1992
INVENTOR(S) : Klaus Kaluza, et. al.

It is certified that error appears in the above-indentified patent and that said Letters Patent is hereby corrected as shown below:

Column 4, line 24, change "Hcl" to --HCl --.
                   change "0.06%" to --0.01% --.

Column 5, line 3, Claim 5, following "consisting of", the text presented herein should read:

```
-- 5'-CA CCGGCG-3'    5'CA CCGGTG-3'    5'-CG CCGGCG-3'
   3'-GTGGCC GC-5'    3'-GTGGCC AC-5'   3'-GCGGCC GC-5' ; and

5'-CG CCGGTG-3'
   3'-GCGGCC AC-5'  --.
```

Signed and Sealed this

First Day of February, 1994

Attest:

BRUCE LEHMAN

Attesting Officer    Commissioner of Patents and Trademarks